US010499868B2

(12) United States Patent
Akiyama et al.

(10) Patent No.: US 10,499,868 B2
(45) Date of Patent: Dec. 10, 2019

(54) X-RAY DIAGNOSTIC APPARATUS AND MEDICAL IMAGE DIAGNOSTIC SYSTEM

(71) Applicant: TOSHIBA MEDICAL SYSTEMS CORPORATION, Otawara-Shi (JP)

(72) Inventors: Masaki Akiyama, Otawara (JP); Yoshimasa Kobayashi, Nasushiobara (JP); Jun Sakakibara, Otawara (JP); Keisuke Nakamura, Utsunomiya (JP); Satoru Ohishi, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 364 days.

(21) Appl. No.: 15/388,150

(22) Filed: Dec. 22, 2016

(65) Prior Publication Data

US 2017/0181720 A1 Jun. 29, 2017

(30) Foreign Application Priority Data

Dec. 24, 2015 (JP) .................................. 2015-252214
Dec. 21, 2016 (JP) .................................. 2016-247690

(51) Int. Cl.
*A61B 6/00* (2006.01)
*A61B 6/04* (2006.01)
*A61B 6/12* (2006.01)

(52) U.S. Cl.
CPC .......... *A61B 6/5205* (2013.01); *A61B 6/0407* (2013.01); *A61B 6/12* (2013.01);
(Continued)

(58) Field of Classification Search
CPC ....... A61B 6/5205; A61B 6/0407; A61B 6/12; A61B 6/4441; A61B 6/466; A61B 6/467; A61B 6/10; A61B 6/02
See application file for complete search history.

(56) References Cited

U.S. PATENT DOCUMENTS

| 2005/0020911 A1* | 1/2005 | Viswanathan ........... A61B 6/12 600/424 |
| 2005/0070792 A1 | 3/2005 | Mizukoshi et al. |

(Continued)

FOREIGN PATENT DOCUMENTS

| JP | 2001-120525 | 5/2001 |
| JP | 2005-95513 | 4/2005 |

(Continued)

*Primary Examiner* — Paula J Stice
(74) *Attorney, Agent, or Firm* — Oblon, McClelland, Maier & Neustadt, L.L.P.

(57) ABSTRACT

According to one embodiment, an X-ray diagnostic apparatus includes an imaging apparatus, processing circuitry and permission input circuitry. The imaging apparatus includes an imaging system performing X-ray imaging of an object, and a bed on which the object is placed. The processing circuitry accepts an instruction to cause the imaging apparatus to perform a operation, and notifies a content of the operation relating to the accepted instruction to a first user. The permission input circuitry accepts information indicating permission of the operation from the first user who has confirmed the content of the operation. The processing circuitry causes the imaging apparatus to perform the operation to more severely restrict the operation compared with after acceptance of information indicating permission of the operation by the permission input circuitry, until the acceptance of information indicating permission of the operation by the permission input circuitry.

19 Claims, 7 Drawing Sheets

(52) U.S. Cl.
CPC ............ *A61B 6/4441* (2013.01); *A61B 6/466* (2013.01); *A61B 6/467* (2013.01); *A61B 6/56* (2013.01)

(56) References Cited

U.S. PATENT DOCUMENTS

| | | |
|---|---|---|
| 2011/0170668 A1 | 7/2011 | Ozawa et al. |
| 2012/0243666 A1* | 9/2012 | Lenchig, Jr. ............ A61B 6/08 378/204 |
| 2016/0029981 A1* | 2/2016 | Van Dijk ................ A61B 6/06 600/424 |

FOREIGN PATENT DOCUMENTS

| | | |
|---|---|---|
| JP | 2005-130929 | 5/2005 |
| JP | 2011-142964 | 7/2011 |
| JP | 2015-37572 | 2/2015 |
| WO | WO 2009/137410 A1 | 11/2009 |

\* cited by examiner

X-RAY DIAGNOSTIC APPARATUS AND MEDICAL IMAGE DIAGNOSTIC SYSTEM

CROSS-REFERENCE TO RELATED APPLICATIONS

This application claims the benefit of priority of Japanese Patent Application No. 2015-252214, filed Dec. 24, 2015, and Japanese Patent Application No. 2016-247690, filed Dec. 21, 2016, the entire contents of all of which are incorporated herein by reference.

FIELD

Embodiments described herein relate generally to an X-ray diagnostic apparatus and a medical image diagnostic system.

BACKGROUND

When performing catheter treatment, a user may perform manipulation by causing an X-ray fluoroscopic image and an X-ray radiographic image (hereafter, referred to as a captured image), which are based on X-ray imaging by an X-ray diagnostic apparatus, to be displayed during manipulation, and confirming the position of a device such as a catheter and a guide wire which are depicted on a captured image such as a fluoroscopic image.

As a technology to support this type of manipulation, there is for example a remote catheter system. According to the remote catheter system, since the operator can remotely control the device, it is possible to reduce X-ray exposure of the operator.

By the way, when the operator remotely controls the device by using the remote catheter system, the operator may further remotely control the X-ray diagnostic apparatus. In this case, the operator can adjust an X-ray imaging region and an X-ray imaging direction by remotely controlling a remote control target, such as an imaging system and a bed of the X-ray diagnostic apparatus, so that a captured image of his/her own desire is obtained.

However, when the operator remotely controls the X-ray diagnostic apparatus, it is difficult for the operator to accurately grasp the positional relationship between a remote control target, and a member or a human including the object (hereinafter referred to as an obstacle), which is located in the vicinity of the target.

For this reason, when the operator remotely controls the X-ray diagnostic apparatus, there is a risk that a remote control target comes into contact with an obstacle, which is highly dangerous.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an X-ray diagnostic apparatus and a medical image diagnostic system according to embodiments of the present invention with reference to the drawings.

In general, according to one embodiment, an X-ray diagnostic apparatus includes an imaging apparatus, processing circuitry and permission input circuitry. The imaging apparatus includes an imaging system configured to perform X-ray imaging of an object, and a bed on which the object is placed. The processing circuitry is configured to accept an instruction to cause the imaging apparatus to perform a operation. And the processing circuitry is configured to notify a content of the operation relating to the accepted instruction to a first user. The permission input circuitry is configured to accept information indicating permission of the operation from the first user who has confirmed the content of the operation. The processing circuitry is further configured to cause the imaging apparatus to perform the operation so as to more severely restrict the operation compared with after acceptance of information indicating permission of the operation by the permission input circuitry, until the acceptance of information indicating permission of the operation by the permission input circuitry.

Figure 1:
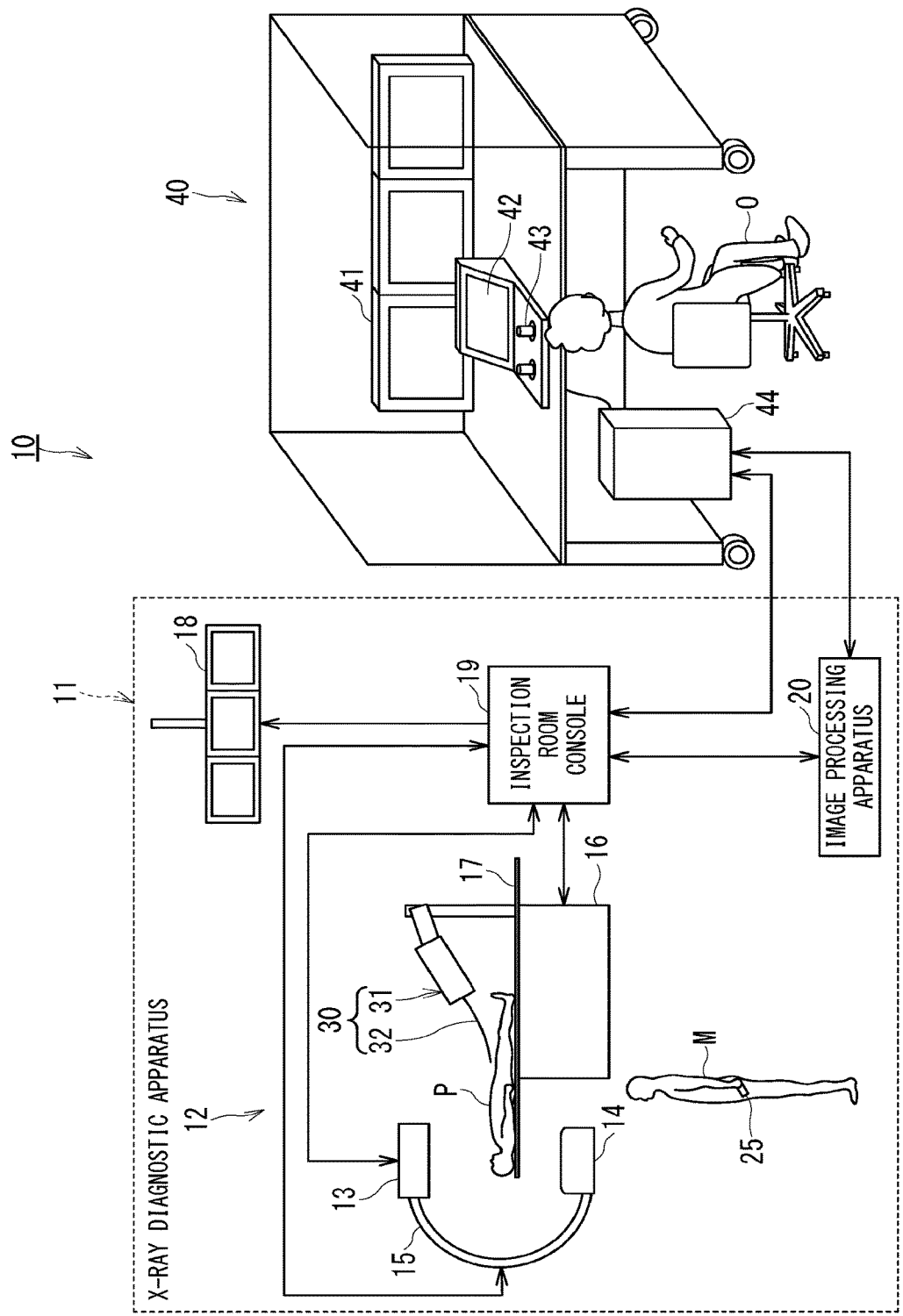
FIG. 1 is a block diagram to show an example of a medical image diagnostic system which includes an X-ray diagnostic apparatus according to a first embodiment of the present invention.

FIG. 1 is a block diagram to show an example of a medical image diagnostic system 10 which includes an X-ray diagnostic apparatus 11 according to a first embodiment of the present invention.

The X-ray diagnostic apparatus 11, which is configured as, for example, an X-ray angiography apparatus, includes an imaging apparatus 12 and an image processing apparatus 20. The imaging apparatus 12 of the X-ray diagnostic apparatus 11, which is commonly installed in an inspection room, is configured to create X-ray projection data relating to an object P. The image processing apparatus 20, which is installed in, for example, an operation room adjacent to the inspection room, is configured to create and display an X-ray captured image based on the X-ray projection data. Note that the image processing apparatus 20 may be installed in the inspection room where the imaging apparatus 12 is installed. In the present embodiment, the imaging apparatus 12 is operated in the presence of a medical engineer M (first user) of the inspection room.

The medical image diagnostic system 10 includes a remote catheter 30 and a remote console 40 as well as the X-ray diagnostic apparatus 11. The remote catheter 30 and the remote console 40 constitute a so-called remote catheter system. In the present embodiment, an operator O (second user) who remotely controls a device 32 in the object P by controlling the remote console 40 is a user other than the medical engineer M.

In the present embodiment, the operator O can operate the imaging apparatus 12 via the remote console 40. Operations of the imaging apparatus 12 include, for example, movement of an imaging system, movement of a bed 16 and a tabletop 17, execution of X-ray imaging by the imaging system, injection control of contrast medium by an injector not shown, and other various operations. Nevertheless, since the operator O originally stays at a site remote from the inspection room, or since, even if the remote console 40 is present in the inspection room, the operator's view is obstructed by a protection board of the remote console 40, it is difficult for the operator to confirm present conditions in the surrounding of the imaging apparatus 12 in detail.

For that reason, when a user other than the medical engineer M, such as the operator O, remotely controls the imaging apparatus 12, it is difficult for the user other than the medical engineer M, such as the operator O, to accurately grasp positional relationships between the operation target by remote control, and obstacles (members and humans including the object P) which are located in the vicinity of the target. The obstacles include, for example, cables located in the vicinities of the imaging system and the bed 16, and instruments such as an injector for injecting a contrast medium. Moreover, there is a case in which a drape covering the object P placed on the bed 16 hangs down from the tabletop 17 to the surface of the floor so that obstacles are hidden by the drape to become not visible. For this reason, when the operator O remotely controls the imaging apparatus 12 to make it perform a predetermined operation, the predetermined operation may endanger obstacles.

The case in which a predetermined operation endangers an obstacle includes a case in which an operation target comes into contact of the obstacle. In such a case, the predetermined operation includes, for example, movement of the imaging system, and movement of the bed 16 or the tabletop 17. Where, the movement includes translational and rotational movements. In this case, it is preferable that such a movement instruction by the operator O is permitted only when the operation target and an obstacle do not come into contact with each other. Besides, the case in which a predetermined operation may endanger an obstacle includes a case in which the predetermined operation is execution of imaging by the imaging system, and an item as an obstacle to be protected from X-ray exposure is located in the vicinity of the imaging system. In this case, it is preferable to avoid actual execution of an execution instruction of imaging by the operator O.

Therefore, when the operator O remotely controls the imaging apparatus 12 to make it perform a predetermined operation, it is important to prevent that the predetermined operation endangers obstacles.

Accordingly, in the X-ray diagnostic apparatus 11 according to the present embodiment, among the operations by the imaging apparatus 12, a predetermined operation when instruction by the operator O is accepted is executed after permission by the medical engineer M is given. Therefore, an input unit through which the medical engineer M gives such permission to an inspection room console 19 is provided in the inspection room. FIG. 1 shows an example in which the medical engineer M carries a permission button 25 as an example of the input unit with which the medical engineer M gives execution permission of a predetermined operation. Note that the permission button 25 is manipulated by the medical engineer M to provide information indicating permission of a predetermined operation to the inspection room console 19. The permission button 25 may be provided on a C-arm 15, a wall surface of the inspection room, or the like, or on the inspection room console 19.

The imaging apparatus 12 of the X-ray diagnostic apparatus 11 includes an X-ray detector 13, an X-ray source 14, a C-arm 15, a bed 16, a tabletop 17 of the bed 16, a display 18, and an inspection room console 19.

The X-ray detector 13 is provided at one end of the C-arm 15 so as to be opposed to the X-ray source 14 with the object P supported by the tabletop (for example, a catheter table, etc.) 17 of the bed 16 being interposed therebetween. The X-ray detector 13, which is made up of a flat plane detector (FPD), detects X-rays which are radiated to the X-ray detector 13 passing through the object P, and outputs projection data of X-ray based on the detected X-rays. This projection data is provided to the image processing apparatus 20 via the inspection room console 19. Note that the X-ray detector 13 may include an image intensifier, a TV camera, or the like.

The X-ray source 14, which is provided at the other end of the C-arm 15, includes an X-ray bulb and an X-ray aperture. The X-ray aperture is, for example, an X-ray irradiation field aperture made up of a plurality of lead blades. The X-ray aperture is controlled by the inspection room console 19 to adjust the irradiation range of X-ray radiated from an X-ray tube bulb.

The C-arm 15 holds the X-ray detector 13 and the X-ray source 14 as a unit body. As a result of the C-arm 15 being controlled by the inspection room console 19 to be driven, the X-ray detector 13 and the X-ray source 14 move as a unit body around the object P. The X-ray detector 13, the X-ray source 14, and the C-arm 15 constitute an imaging system that captures an X-ray image of the object P.

The X-ray imaging by the imaging system includes so-called fluoroscopy and radiography. Fluoroscopy is X-ray imaging to acquire an image by X-ray irradiation with a weaker X-ray irradiation intensity compared with radiography. For that reason, although the resolution of a fluoroscopic image acquired by fluoroscopy is lower than that of a radiographic image acquired by radiography, X-ray dose to which the object P is exposed in fluoroscopy is lower than in radiography. Therefore, fluoroscopy is suitable when it is desirable to confirm an X-ray image of the object P in an animating manner in real time. On the other hand, although X-ray dose to which the object P is exposed is higher, the image quality is clearer in radiography than in fluoroscopy. In the following description, fluoroscopy and radiography are conveniently referred to as X-ray imaging, and an X-ray fluoroscopic image and an X-ray radiographic image based on X-ray imaging are conveniently referred to as a captured image.

Moreover, when the X-ray diagnostic apparatus 11 is used as an angiography apparatus, the X-ray diagnostic apparatus 11 may be of a biplane type having two lines of imaging system which is made up of the X-ray detector 13, the X-ray source 14, and the C-arm 15 and captures an X-ray image of the object P. In the case of biplane type, the X-ray diagnostic apparatus 11 can acquire a biplane image (F (frontal) side image and L (lateral) side image) by causing an X-ray beam to be radiated separately from each of two directions of the F side having a floor mounted C-arm and the L side having a ceiling travelling Q-arm.

The bed 16, which is placed on the floor, has a tabletop 17. The bed 16 is controlled by the inspection room console 19 to cause the tabletop 17 to move in the horizontal and vertical directions, and to rotate (roll).

Figure 2:
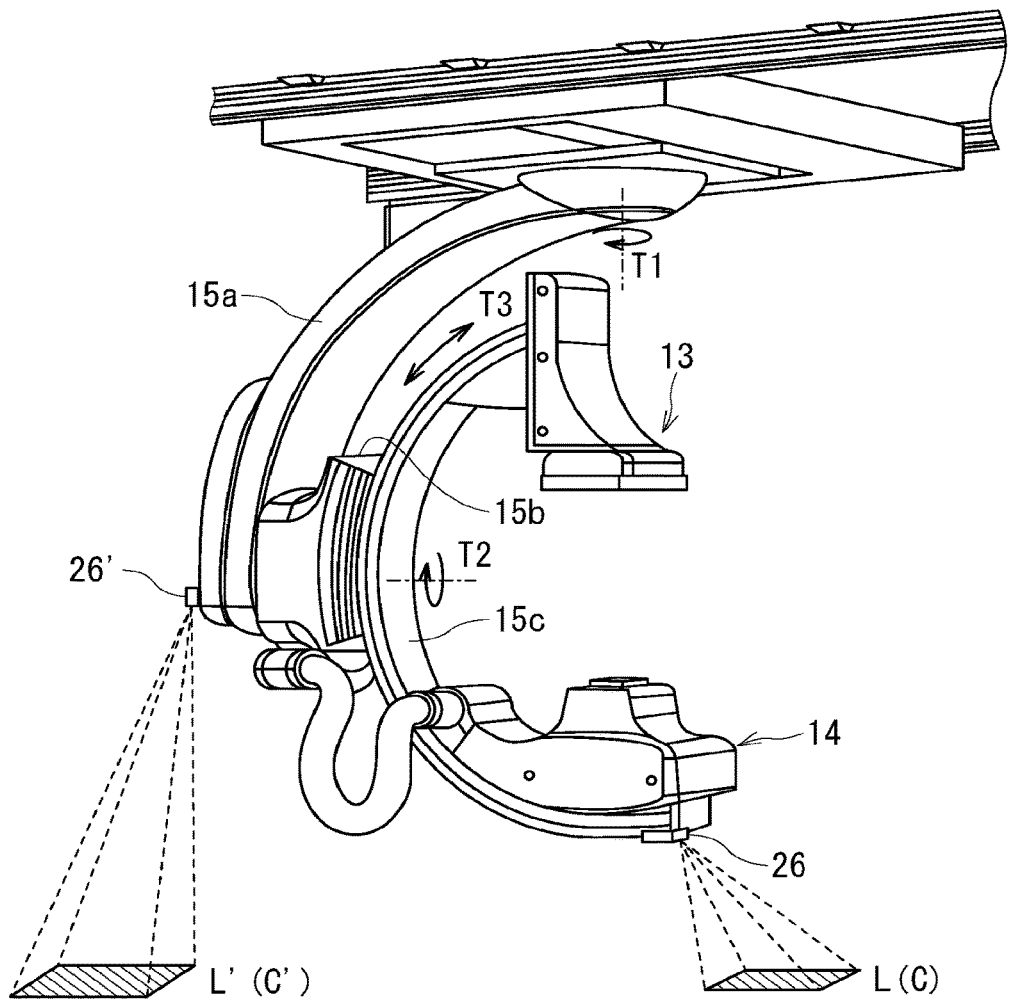
FIG. 2 is an explanatory diagram to show one example of a light emitting portion provided in the C-arm.

FIG. 2 is an explanatory diagram to show one example of a light emitting portion 26 provided in the C-arm 15.

A light emitting portion 26 which emits light toward the moving direction by a predetermined operation may be provided on an operation target of the predetermined operation of the imaging apparatus 12. As described above, the predetermined operation includes, for example, movement of the imaging system, or movement of the bed 16 or the tabletop 17, execution of imaging by the imaging system, and the like. Accordingly, among the predetermined operations, so as to inform the medical engineer M of contents of operation relating to movement, a light emitting portion 26 which is made up of for example an LED is provided in at least one location of at least one of the imaging system of the imaging apparatus 12 and the bed 16.

For example, consider a case in which the C-arm 15 is a ceiling suspension type and is made up of a suspension arm 15a, a rotating mechanism 15b, and a main arm 15c (see FIG. 2). In this case, the entire C-arm 15 rotates about the vertical axis T1 (see FIG. 2) of a vertical-axis rotating mechanism. Moreover, the main arm 15c is rotated about a rotation axis T2 with respect to the suspension arm 15a by the rotating mechanism 15b. Further, the main arm 15c may be configured to be movable in sliding with respect to the rotating mechanism 15b. In this case, the main arm 15c moves in a circular arc along a circular-arc direction T3 of the main arm 15c.

When the light emitting portion 26 is provided in the main arm 15c, the light emitting portion 26 presents a sliding track along the ceiling surface to which the main arm 15c is mounted, and a vertical-axis rotating track of the main arm 15c associated with the rotation about the vertical axis T1 (see FIG. 2) of the vertical-axis rotating mechanism. In this case, the light emitting portion 26 is proved at, for example, a lower end of the main arm 15c. The light emitting portion 26 emits laser light to a presentation plane L for presenting a track of the main arm 15c to the medical engineer M, which is targeted for a track plane C which is a projection of the sliding track of the main arm 15c and the vertical-axis rotating track of the main arm 15c onto the floor surface. The presentation plane L may be identical with the track plane C or may be included in the track plane C. Moreover, the light emitting portion 26 may be provided at an upper end of the main arm 15c. In this case, the light emitting portion 26 emits laser light to a presentation plane for presenting the track of main arm 15c to the medical engineer M, which is targeted for a track plane which is a projection of the sliding track of the main arm 15c and the vertical-axis rotating track of the main arm 15c to the ceiling surface.

Note that the imaging system may be provided in the suspension arm 15a with a light emitting portion 26' together with the light emitting portion 26, or in place of the light emitting portion 26. In this case, the light emitting portion 26' emits laser light to a presentation plane L' for presenting the track of the main arm 15c to the medical engineer M, which is targeted for a track plane C' which is a projection of the sliding track of the main arm 15c and the vertical-axis rotating track of the main arm 15c onto the floor surface (the presentation plane L' may be the same as the track plane C', or may be included in the track plane C').

Similarly, the light emitting portion 26 that emits light toward the moving direction by the predetermined operation may be provided in the bed 16 and the tabletop 17 as well.

The display 18, which is made up of one or more display regions, is controlled by the inspection room console 19 to display information and fluoroscopic image to show the content of the predetermined operation. The display 18 is made up of a general display output apparatus such as a liquid crystal display and an OLED (Organic Light Emitting Diode) display, etc.

The inspection room console 19 is controlled by the image processing apparatus 20 to execute X-ray imaging of the object P thereby creating projection data by controlling the X-ray detector 13, and to provide the projection data to the image processing apparatus 20. The inspection room console 19 is controlled by the image processing apparatus 20 to create, for example, projection data before and after the administration of contrast medium, respectively to provide the projection data to the image processing apparatus 20.

The inspection room console 19 may be, for example, a satellite console which is movable on the floor surface of the inspection room. The inspection room console 19 may become an obstacle for the predetermined operation of the imaging apparatus 12.

Further, when the X-ray diagnostic apparatus 11 is configured to be capable of rotation DSA (Digital Subtraction Angiography), the inspection room console 19 is controlled by the image processing apparatus 20 to execute rotation DSA thereby creating projection data before and after administration of contrast medium, respectively, and to provide the projection data to the image processing apparatus 20. In the rotation DSA, image data (mask image data) before the contrast medium is injected and image data (contrast image data) after the contrast medium is injected are created respectively, for the same site of the object P. When the rotation DSA is possible, the X-ray diagnostic apparatus 11 can also acquire a 3-dimensional blood-vessel image (3D angiogram) based on the contrast image data and the mask image obtained by the rotation DSA.

The inspection room console 19 includes at least a processor and memory circuitry. The inspection room console 19 is controlled by the image processing apparatus 20 according to a program stored in the memory circuitry to execute X-ray imaging such as fluoroscopy of the object P by controlling the imaging system, thus outputting the projection data.

Note that although FIG. 1 shows an example in which the inspection room console 19 and the image processing apparatus 20 are connected with wire, the inspection room console 19 and the image processing apparatus 20 may be connected so as to be able to transmit/receive data via a network.

Moreover, the X-ray diagnostic apparatus 11 may include an injector not shown. In this case, the injector is controlled by the inspection room console 19 to inject a contrast medium via a device 32 of the remote catheter 30 inserted into an affected part of the object P. The timings of injection and stopping of the contrast medium, and the density and injection rate of the contrast medium are automatically controlled by the inspection room console 19. Moreover, the injector may not be controlled by the inspection room console 19, and for example it may accept an instruction by the medical engineer M via an input portion provided in the injector, or accept an instruction by the operator O via the remote console 40, and inject a contrast medium at a density, rate, and timing according to the instruction.

On the other hand, the remote catheter 30 of the remote catheter system as an example of the remote control system includes a robot arm 31 and a device 32 and is controlled by the remote console 40 to insert the device 32 into a predetermined site (for example, an affected part) of the object P. Moreover, the remote catheter 30 may be configured to be capable of remote controlling a plurality of devices 32.

The remote console 40 includes display input circuitry 41 and 42, remote input circuitry 43 for remotely controlling the device 32 of the remote catheter 30, and a control apparatus 44.

The display input circuitry 41 and 42 include a display, and a touch sensor provided in the vicinity of the display. The display is made up of for example a general display output apparatus such as a liquid crystal display and an OLED (Organic Light Emitting Diode) display. The touch sensor provides information of instruction position on the touch sensor by the user to the processing circuitry of the control apparatus 44. For example, if it is made up of a projection-type, electrostatic capacitive panel, the touch sensor has an array of electrodes disposed longitudinally and laterally. In this case, the touch sensor can acquire a contact position based on the output change of the electrode array corresponding to changes of electrostatic capacity in the vicinity of the contact point of a contact object.

The display of the display input circuitry 41 is controlled by the processing circuitry of the control apparatus 44 to display, for example, images similar to those of the display 18.

The display of the display input circuitry 42 is controlled by the processing circuitry of the control apparatus 44 to display, for example, information relating to a control target device of the remote input circuitry 43.

The remote input circuitry 43 is made up of general pointing devices such as a trackball or a trackball mouse, a keyboard, a touch panel, a ten key, voice input circuitry, and eye-gaze input circuitry, and a hand switch for instructing the timing of X-ray exposure. The remote input circuitry 43 is operated by the operator O to output a signal for remotely controlling the device 32 via the control apparatus 44 with wired or wireless communication to the remote catheter 30 via the control apparatus 44. Moreover, the remote input circuitry 43 is operated by the operator O to provide a signal for remotely controlling the imaging apparatus 12, such as a signal for causing the imaging apparatus 12 to perform a predetermined operation, directly to the inspection room console 19 via the control apparatus 44, or indirectly via the image processing apparatus 20, to the inspection room console 19.

The control apparatus 44 includes at least a processor and memory circuitry. The processing circuitry of the control apparatus 44 cooperates with the image processing apparatus 20 according to a program stored in the memory circuitry. For example, the processing circuitry of the control apparatus 44 provides information on feed movement of the device 32 to the image processing apparatus 20. Moreover, the processing circuitry of the control apparatus 44 provides information on instruction by the operator O for causing the imaging apparatus 12 to perform a predetermined operation directly, or indirectly via the image processing apparatus 20, to the inspection room console 19.

Figure 3:
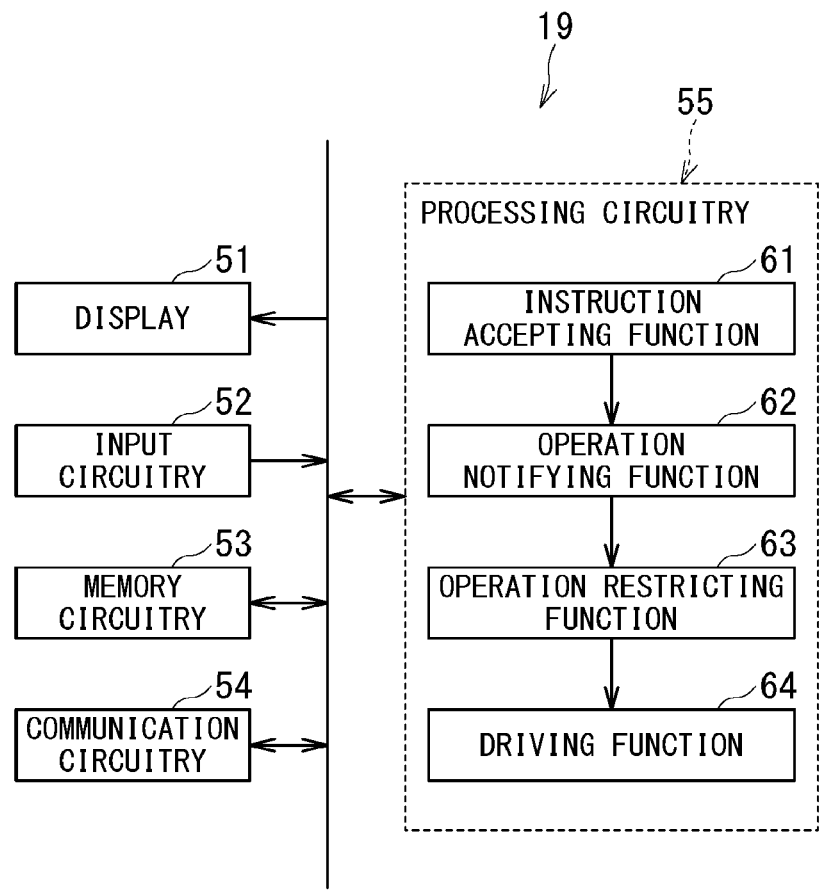
FIG. 3 is a block diagram to show an example configuration of the inspection room console.

FIG. 3 is a block diagram to show an example configuration of the inspection room console 19.

The inspection room console 19 includes a display 51, input circuitry 52, memory circuitry 53, communication circuitry 54, and a processing circuitry 55.

The display 51 is made up of, for example, a general display output apparatus such as a liquid crystal display and an OLED (Organic Light Emitting Diode) display, and displays various information such as information to show the content of the predetermined operation according to control by the processing circuitry 55.

The input circuitry 52 is made up of, for example, general input apparatuses such as a keyboard, a touch panel, a trackball, a ten key, voice input circuitry, and eye-gaze input circuitry. The input circuitry 52 outputs an input signal according to the manipulation by the medical engineer M to the processing circuitry 55.

The memory circuitry 53 is configured to include a processor-readable recording medium, such as a magnetic or optical recording medium, or a semiconductor memory. Part or all of the program and data in the recording media may be configured to be downloaded by communication via an electronic network. The communication circuitry 54 implements various protocols for information communication according to the form of the network. The communication circuitry 54 connects the inspection room console 19 with the image processing apparatus 20 and the control apparatus 44 of the remote console 40 according to the various protocols. For this connection, it is possible to apply an electric connection via an electronic network, or the like. Here, the electronic network, which implies whole information communication networks utilizing telecommunication technologies, includes, besides wired/wireless LAN (Local Area Network) and the Internet network, telephone communication channel networks, optical fiber communication networks, cable communication networks, satellite communication networks, and the like. For example, the processing circuitry 55 may acquire medical 3-dimensional image data (hereinafter, referred to as volume data) from an image server, etc. via a network.

The processing circuitry 55 is a processor for executing processing to support secure remote control of the X-ray diagnostic apparatus 11 by the operator O of the device 32 by reading and executing a program stored in the memory circuitry 53.

As shown in FIG. 3, the processing circuitry 55 implements an instruction accepting function 61, an operation notifying function 62, an operation restricting function 63, and a driving function 64. Each of these functions is stored in the memory circuitry 53 in the form of program, respectively. Details of the operation of each of the functions 61 to 64 will be described below with reference to FIGS. 5 and 6.

Figure 4:
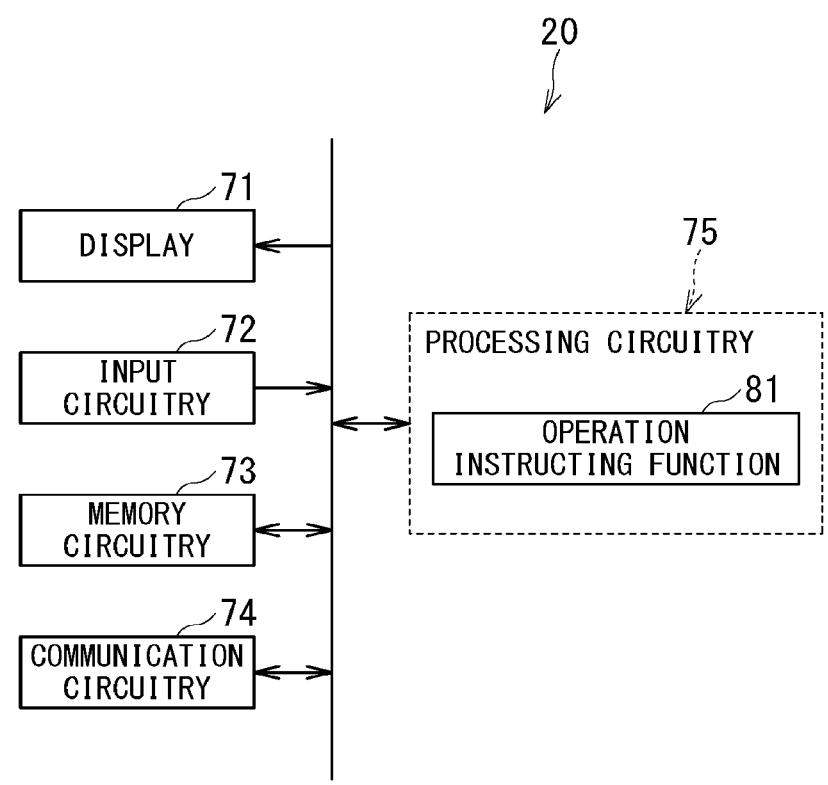
FIG. 4 is a block diagram to show an example configuration of the image processing apparatus.

FIG. 4 is a block diagram to show an example configuration of the image processing apparatus 20.

The image processing apparatus 20 includes a display 71, input circuitry 72, memory circuitry 73, a communication circuitry 74, and a processing circuitry 75.

The display 71 is made up of, for example, a general display output apparatus such as a liquid crystal display and an OLED (Organic Light Emitting Diode) display, and displays various information such as information to show the content of the predetermined operation according to the control by the processing circuitry 75.

The input circuitry 72 is made up of, for example, general input apparatuses such as a keyboard, a touch panel, a trackball, a ten key, voice input circuitry, and eye-gaze input circuitry, and outputs an input signal according to the manipulation by a user in the operation room including the medical engineer M and the operator O to the processing circuitry 75.

The memory circuitry 73 is configured to include a processor-readable recording medium, such as a magnetic or optical recording medium, or a semiconductor memory. Part or all of the program and data in the recording media may be configured to be downloaded by communication via an electronic network. The communication circuitry 74 implements various protocols for information communication according to the form of the network. The communication circuitry 74 connects the image processing apparatus 20 with the inspection room console 19 and the control apparatus 44 of the remote console 40 according to the various protocols. For this connection, it is possible to apply an electric connection via an electronic network, or the like.

The processing circuitry 75 is a processor for executing processing to support secure remote control of the X-ray diagnostic apparatus 11 by the operator O of the device 32 in cooperation with the inspection room console 19 by reading and executing a program stored in the memory circuitry 73.

As shown in FIG. 4, the processing circuitry 75 implements an operation instructing function 81. The operation instructing function 81 is stored in the memory circuitry 53 in the form of program. The operation instructing function 81 executes X-ray imaging of an object P by controlling the imaging apparatus 12 via the inspection room console 19 based on an imaging plan specified by a medical engineer M etc. via the input circuitry 72. Moreover, the operation instructing function 81 causes the imaging apparatus 12 to execute X-ray fluoroscopy based on the instruction by the medical engineer M etc. via the input circuitry 72. This operation instructing function 81 may be implemented by the processing circuitry 55 of the inspection room console 19.

Figure 5:
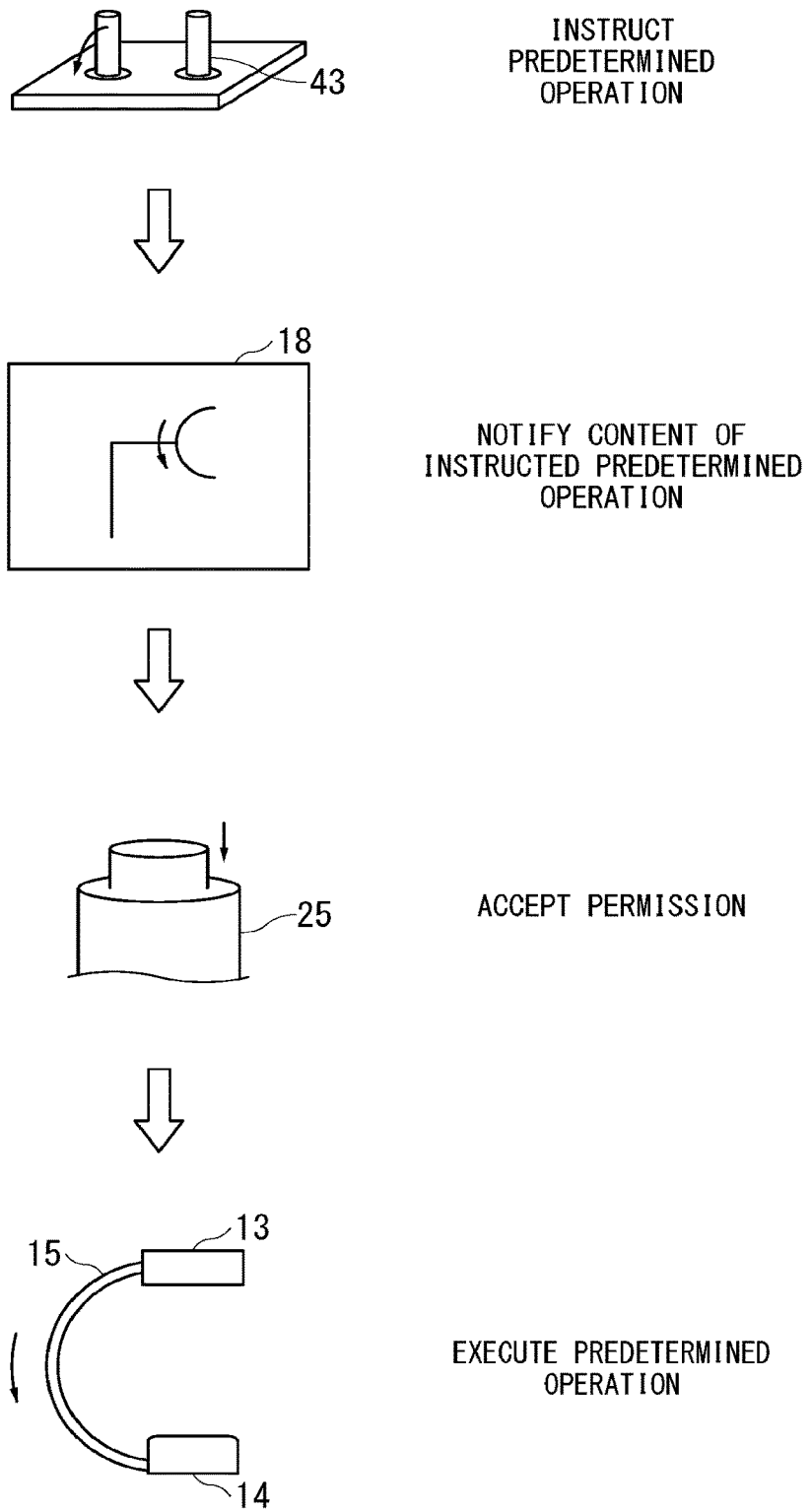
FIG. 5 is a diagram to explain the procedure for the operator of the device to safely remote-control the X-ray diagnostic apparatus.
Figure 6:
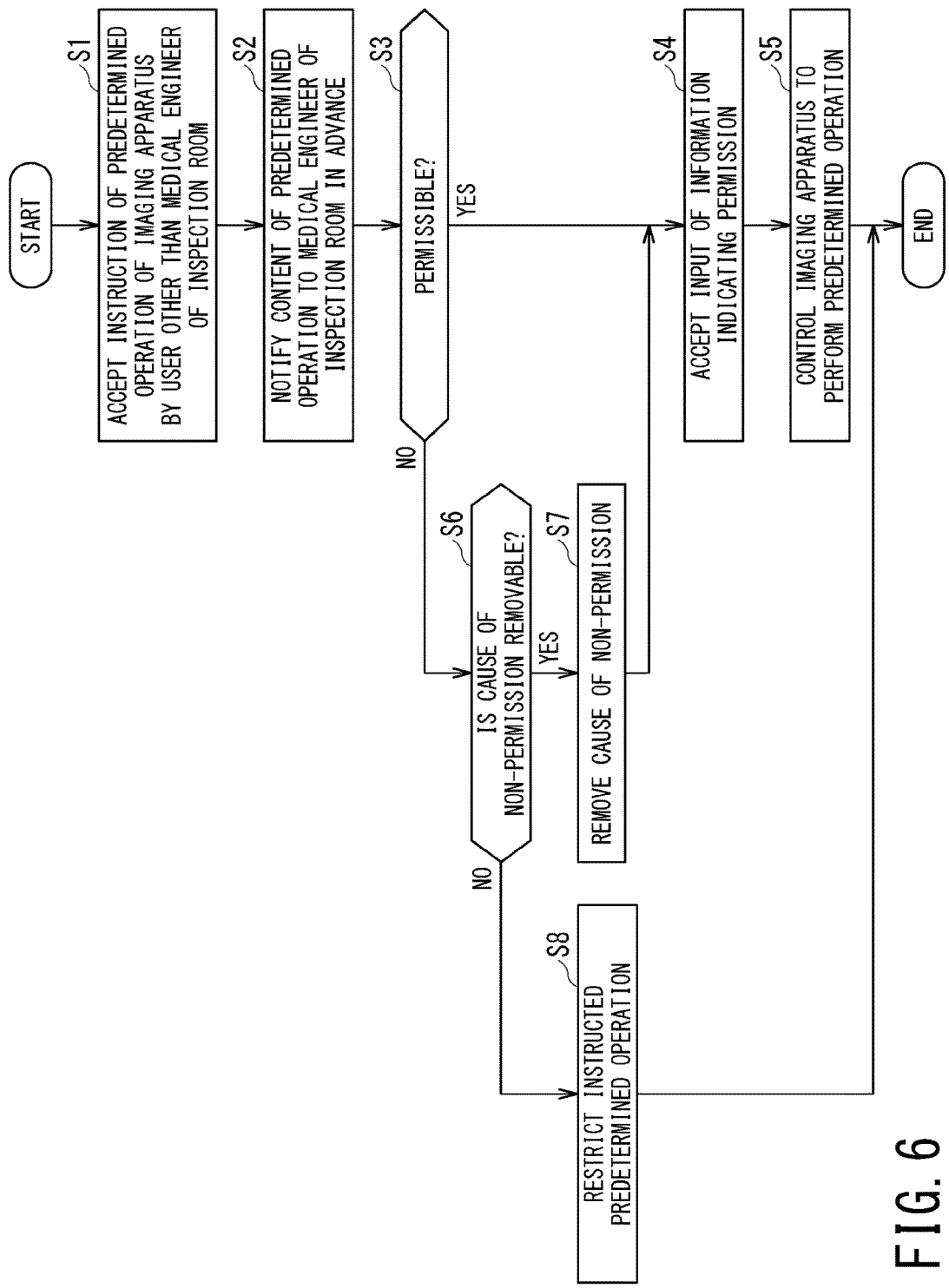
FIG. 6 is a flowchart to show an example of the procedure when performing the processing to support the secure remote control of the X-ray diagnostic apparatus by the operator of the device, by the processing circuitry shown in FIG. 3.

FIG. 5 is a diagram to explain the procedure for the operator O of the device 32 to safely remote-control the X-ray diagnostic apparatus 11. Moreover, FIG. 6 is a flow-chart to show an example of the procedure when performing the processing to support the secure remote control of the X-ray diagnostic apparatus 11 by the operator O of the device 32, by the processing circuitry 55 shown in FIG. 3. In FIG. 6, a reference symbol S with a number indicates each step of the flowchart.

Note that the following description shows an example case in which the user other than the medical engineer M of the inspection room is an operator O, and the predetermined operation is sliding operation of the C-arm 15 along T3 direction. The user other than the medical engineer M of the inspection room may be a user of the image processing apparatus 20, and in this case, the user may provide a signal for remotely controlling the imaging apparatus 12 from the operation room, such as a signal for causing the imaging apparatus 12 to perform the predetermined operation, to the instruction accepting function 61 of the inspection room console 19 via the input circuitry 52 of the image processing apparatus 20.

In step S1, the instruction accepting function 61 accepts an instruction to cause the imaging apparatus 12 to perform a predetermined operation from the operator O (user other than the medical engineer M of the inspection room) via the remote input circuitry 43. The illustration at the top of FIG. 5 shows an example control of the control lever by the operator O in the case in which the remote input circuitry 43 includes a control lever, and control to tilt the control lever to the closer or further side is assigned to an instruction of sliding operation along the T3 direction of the C-arm 15.

The X-ray diagnostic apparatus 11 according to the present embodiment is configured such that even if an instruction to cause the imaging apparatus 12 to perform a predetermined operation is remotely given by anyone other than the medical engineer M, the relevant operation is not performed immediately.

To be specific, first, in step S2, the operation notifying function 62 notifies the content of the predetermined operation relating to the instruction accepted by the instruction accepting function 61 to the medical engineer M of the inspection room.

The method of notification may be a method of displaying an image showing that an operation target of a predetermined operation performs the predetermined operation, on at least one of the displays 18, 51, and 71 provided at a position which is visible to the medical engineer M. Moreover, when the X-ray diagnostic apparatus 11 includes a light emitting portion 26, the content of the predetermined operation may be notified via the light emitting portion 26. Further, the method may be a method of using voice via a speaker, which is not shown and provided in the inspection room, or any combination of an image, light, and voice.

The illustration in the second stage from the top of FIG. 5 shows an example in which the operation notifying function 62 notifies the content of the predetermined operation accepted by the instruction accepting function 61 to the medical engineer M by creating an image to show that the C-arm 15 (operation target of the predetermined operation) performs sliding operation (the predetermined operation), and causing this image to be displayed on the display 18. This image preferably displays text information and an image (for example, an arrow mark), etc. to show the direction and the amount of movement (amount of rotation) in and by which the operation target is moved by the predetermined operation.

Moreover, the operation notifying function 62 may display, as this image, animation corresponding to the predetermined operation on at least one of the displays 18, 51, and 71 by using a rendering image obtained by rendering 3-dimensional image data of the operation target. In this case, 3-dimensional image data and the images after rendering processing of the C-arm 15, the bed 16, and the remote catheter 30, etc. as the operation target may be stored in advance in the memory circuitry 53, or acquired via a network. When animation display of an image having a stereoscopic effect such as a rendering image is performed, the medical engineer M can grasp the content of a predetermined operation more instinctively since he/she can confirm operation simulation of the operation target.

As described above, in this point, the operation restricting function 63 has not relieved the restriction of the predetermined operation yet, and the predetermined operation has not been permitted.

Next, in step S3, the medical engineer M confirms safety of the predetermined operation for example by confirming obstacles around the imaging system to determine whether or not the predetermined operation notified by the operation notifying function 62 is permissible.

When permissible, in step S4, the operation restricting function 63 accepts information indicating permission and inputted by the medical engineer M, and relieves the restriction of the predetermined operation to permit the predetermined operation. At this moment, the medical engineer M can provide information indicating permission to the operation restricting function 63 for example by depressing a permission button 25 (see the illustration in third stage from the top in FIG. 5), or inputting a voice input indicating permission via the input circuitry 52.

Then, in step S5, the driving function 64 is controlled by the operation restricting function 63 to cause the imaging apparatus 12 to perform the predetermined operation which is permitted or restricted by the operation restricting function 63 (see the illustration at the bottom of FIG. 5).

Note that it is also possible that the medical engineer M gives complete permission for the remote control by the operator O by the medical engineer M keeping on depressing the permission button 25, or by the medical engineer M setting complete permission via the input circuitry 52 before starting the procedure shown in FIG. 6. In this case, step S3 is substantially skipped, and the operator O can remotely control the imaging apparatus 12 without feeling any waiting time.

On the other hand, when in step S3, the medical engineer M has determined that the predetermined operation is not permissible, in step S6, the medical engineer M determines whether or not the cause of non-permission is removable. For example, when the cause of non-permission is an obstacle which can be moved with ease, it is determined to be removable, and the cause of non-permission is removed by, for example, removing the obstacle (step S7), causing the process to proceed to step S4. On the other hand, when it is determined that the cause of non-permission cannot be removed, the predetermined operation is more severely restricted by the operation restricting function 63 compared with after acceptance of information indicating permission of the predetermined operation in step S8, and a series of procedures is completed.

Figure 7:
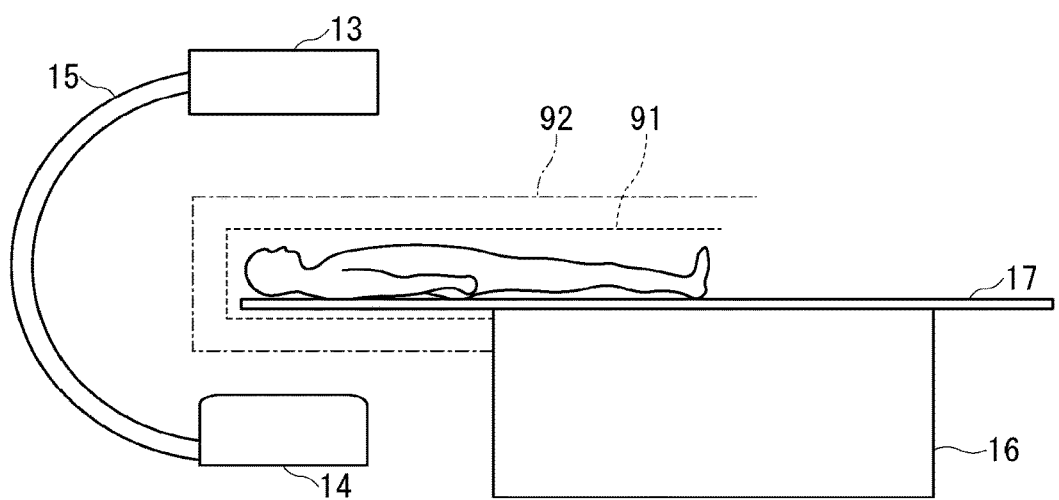
FIG. 7 is a diagram to explain one example of a method of restricting a predetermined operation.

Here, as the method of restricting the predetermined operation by the operation restricting function 63, various methods can be used. FIG. 7 is a diagram to explain one example of the method of restricting the predetermined operation. A first restricting method is not starting (prohibiting) the execution of the predetermined operation until acceptance of information indicating permission of the predetermined operation from the medical engineer M. A second restricting method is executing the predetermined operation in a low speed mode of not more than a predetermined speed so as to decrease the speed of the predetermined operation to be lower compared with after acceptance of information indicating permission of the predetermined operation until acceptance of information indicating permission of the predetermined operation from the medical engineer M.

A third restricting method is enlarging the region in which the speed of the predetermined operation is decreased to be larger compared with after acceptance of information indicating permission of the predetermined operation until acceptance of information indicating permission of the predetermined operation from the medical engineer M. For example, in a region 91 which is very close to the bed 16, the tabletop 17, and the object P as shown in FIG. 7, it is preferable that the predetermined operation is performed carefully even if permission of the medical engineer M has been given.

Accordingly, when information indicating permission of the predetermined operation is accepted from the medical engineer M, the region 91 may be specified to be the region in which the speed of the predetermined operation is decreased. In this case, until acceptance of information indicating permission of the predetermined operation from the medical engineer M, the region in which the speed of the predetermined operation is decreased may be specified to be a region 92 which is larger than the region 91 (see FIG. 7).

A fourth restricting method is decreasing the range to which the imaging apparatus 12 is accessible in the predetermined operation to be smaller compared with after acceptance of information indicating permission of the predetermined operation until acceptance of information indicating permission of the predetermined operation from the medical engineer M. For example, it is safer when the C-arm 15 and others are prohibited from entering the region 91 even if there is permission of the medical engineer M. Accordingly, even when information indicating permission of the predetermined operation is accepted from the medical engineer M, the region 91 may be specified as a region to which the imaging apparatus 12 is not accessible, and other regions as an accessible region. In this case, until acceptance of information indicating permission of the predetermined operation from the medical engineer M, the range to which the imaging apparatus 12 is accessible may be decreased by specifying the region to which the imaging apparatus 12 is not accessible to be the region 92 which is larger than the region 91 (see FIG. 7).

According to the third and fourth restricting methods, since the imaging apparatus 12 can be normally operated outside the range of the region 92 even without permission of the medical engineer M, it is possible to reduce stress felt by the operator O as well as to improve safety relating to interference between instruments compared with the first and second restricting methods.

Moreover, the third and fourth restricting methods can be combined with each other. For example, when information indicating permission is accepted, the region 91 may be specified as a region in which the speed of the predetermined operation is decreased, thereby allowing entrance of instruments, and on the other hand, the region 92 may be specified as a region to which the imaging apparatus 12 is not accessible until acceptance of information indicating permission of the predetermined operation from the medical engineer M.

The method of restricting operation is specified during the procedure shown in FIG. 6 or in advance by at least one of the medical engineer M and the operator O, and stored in the memory circuitry 53 to be utilized by the operation restricting function 63. Further, when a low speed mode is used in the second restricting method, the operation restricting function 63 may cause the operation target to be operated in the low speed mode after waiting for a predetermined time (for example, several seconds) after first presenting information indicating instruction of the predetermined operation, and operation in the low speed mode to the medical engineer M through a voice of alert and an image of alert instead of causing the operation target to operate in the low speed mode immediately after acceptance of the predetermined operation in step S1.

Moreover, the operation restriction by the operation restricting function 63 may already be set to ON at the start of the procedure shown in FIG. 6. In this case, since the instruction accepting function 61 accepts instruction of a predetermined operation from a user other than the medical engineer M till it accepts information indicating permission inputted from the medical engineer M in step S4, the operation restricting function 63 keeps on restricting the predetermined operation.

Note that when the content of manipulation by the operator O to be accepted in step S1 is temporary manipulation (such as tapping of a touch panel), the content of the manipulation, or the predetermined operation assigned to this manipulation may be stored in the memory circuitry 53 until the predetermined operation assigned to the content of this manipulation or this manipulation is permitted.

Moreover, after execution of step S1, or after execution of step S3, when a predetermined time has elapsed, the operation restricting function 63 may rescind the acceptance in step S1 to cancel the predetermined operation. In this case, the operation restricting function 63 may create an image including information indicating that the acceptance of the predetermined operation is rescinded because a predetermined time has elapsed without permission, and cause the image to be displayed on displays 41 and 42. Moreover, when a user other than the medical engineer M of the inspection room is the user of the image processing apparatus 20, the operation restricting function 63 may cause the image to be displayed on a display 51.

According to the procedure described above, the operator O of the device 32 can safely remote-control the X-ray diagnostic apparatus 11.

In the X-ray diagnostic apparatus 11 according to the present embodiment, among operations by the imaging apparatus 12, predetermined operations for which instruction of a user other than the medical engineer M is received are executed after permission by the medical engineer M is obtained. For that reason, when the imaging apparatus 12 is controlled by a user who cannot sufficiently confirm the safety around the imaging apparatus 12, and when the medical engineer M who has confirmed the current conditions around the imaging apparatus 12 determines that there is danger, the execution of the predetermined operation can be readily restricted. Therefore, according to the medical image diagnostic system 10 including the X-ray diagnostic apparatus 11 according to the present embodiment, the operator O of the device 32 can safely remote-control the X-ray diagnostic apparatus 11.

Note that the processing circuitry 55 in the present embodiments is an example of the processing circuitry described in the claims. Moreover, the permission button 25 and the input circuitry 52 in the present embodiment are each one example of a permission input circuitry in the claims.

Moreover, the term "processor" relating to the processing circuitry 55 and 75 of the image processing apparatus 20 and the processing circuitry of the control apparatus 44 of the remote console 40 in the present embodiment refer to circuitry, such as special purpose or general purpose CPUs (Central Processing Units), GPUs (Graphic Processing Units), or ASICs (Application Specific Integrated Circuits), programmable logic devices (for example, SPLDs (Simple Programmable Logic Devices), CPLDs (Complex Programmable Logic Devices), and FPGA (Field Programmable Gate Arrays)), and the like. The processor implements various functions by reading out and executing programs stored in the memory circuitry.

Note that instead of storing programs in the memory circuitry, the programs may be directly incorporated into the circuitry of the processor. In this case, the processor implements each function by reading out and executing each program incorporated in the circuitry. Moreover, although FIG. 3 shows an example in which a single processing circuitry 55 implements each function, each function may be implemented by making up processing circuitry by combining a plurality of separate processors, and executing each program by each processor. Further, when a plurality of processors are provided, the memory medium to store programs may be individually provided for each processor, or one memory circuitry may collectively store programs corresponding to all the functions of the processor.

Note that although some embodiments of the present invention have been described so far, these embodiments are presented by way of examples, and not intended to limit the scope of the invention. These novel embodiments can be practiced in other various forms, and various omissions, substitutions, modifications can be made within a range not departing from the spirit of the invention. These embodiments and variants thereof will be included in the scope and spirit of the invention, and also included in the range of the invention and equivalents thereof set forth in the claims of patent. Further, components belonging to different embodiments may be appropriately combined.

Moreover, in the embodiments of the present invention, although an example of processing in which each step of a flowchart is executed along a time series according to the described order has been shown, the processing may not necessarily be performed along the time series, and may be performed in parallel or individually.

What is claimed is:

1. An X-ray diagnostic apparatus, comprising:
an imaging apparatus including an imaging system and a bed, the imaging system being configured to perform X-ray imaging of an object and being composed of an X-ray source, X-ray detector and a support portion supporting the X-ray source, the bed including a tabletop on which the object is placed;
processing circuitry configured to
accept an instruction to cause the imaging apparatus to perform an operation, the operation being movement of at least one of the imaging system, the bed and the tabletop, and
notify a content of the movement relating to the accepted instruction to a first user; and
permission input circuitry configured to accept information indicating permission of the movement from the first user who has confirmed the content of the movement,
wherein the processing circuitry is further configured to cause the imaging apparatus to perform the movement so as to more severely restrict the movement compared with after acceptance of information indicating permission of the movement by the permission input circuitry, until the acceptance of information indicating permission of the movement by the permission input circuitry.

2. The X-ray diagnostic apparatus according to claim 1, wherein
processing circuitry restricts the movement by increasing a region in which speed of the movement is decreased until the acceptance, compared with said region after the acceptance.

3. The X-ray diagnostic apparatus according to claim 1, wherein
the processing circuitry restricts the movement by decreasing a region in which the imaging system and/or the bed and/or the tabletop is movable until the acceptance, compared with said movable region after the acceptance.

4. The X-ray diagnostic apparatus according to claim 1, wherein
processing circuitry restricts the movement by decreasing a speed of the movement until the acceptance, compared with after the acceptance.

5. The X-ray diagnostic apparatus according to claim 1, wherein
the processing circuitry restricts the movement by not starting the movement until the acceptance of information indicating permission of the movement by the permission input circuitry.

6. The X-ray diagnostic apparatus according to claim 1, wherein
the permission input circuitry is a switch.

7. The X-ray diagnostic apparatus according to claim 1, wherein
processing circuitry notifies the first user of a content of the movement, for which instruction has been accepted, by creating an image indicating that a movement target moves according to the accepted instruction for the movement, and by causing the image to be displayed on a display provided at a position visible to the first user.

8. The X-ray diagnostic apparatus according to claim 7, wherein
the processing circuitry causes animation according to the movement to be displayed on the display by using a rendering image which is obtained by rendering 3-dimensional image data of the movement target.

9. The X-ray diagnostic apparatus according to claim 1, further comprising:
a light emitting portion provided in at least one location of at least one of the imaging system and the bed of the imaging apparatus, wherein
the processing circuitry makes the light emitting portion emit light toward a moving direction of the movement of the movement target from the light emitting portion provided in the movement target of the movement.

10. An X-ray diagnostic apparatus, comprising:
an imaging apparatus including an imaging system configured to perform X-ray imaging of an object, and a bed on which the object is placed;
processing circuitry configured to
accept, from an outside of an inspection room in which the imaging apparatus is provided, an instruction to cause the imaging apparatus to perform an operation, the operation being any one of movement of the imaging system, movement of the bed or a tabletop of the bed, and
notify a content of the movement relating to the accepted instruction to a first user in the inspection room; and
permission input circuitry configured to accept information indicating permission of the movement from the first user who has confirmed the content of the movement,
wherein the processing circuitry is further configured to cause the imaging apparatus to perform the movement so as to more severely restrict the movement compared with after acceptance of information indicating permission of the movement by the permission input circuitry, until the acceptance of information indicating permission of the movement by the permission input circuitry.

11. The X-ray diagnostic apparatus according to claim 10, wherein
processing circuitry restricts the movement by increasing a region in which speed of the movement is decreased until the acceptance, compared with said region after the acceptance.

12. The X-ray diagnostic apparatus according to claim 10, wherein
the processing circuitry restricts the movement by decreasing a region in which the imaging system and/or the bed and/or the tabletop is movable until the acceptance, compared with said movable region after the acceptance.

13. The X-ray diagnostic apparatus according to claim 10, wherein
processing circuitry restricts the movement by decreasing a speed of the movement until the acceptance, compared with after the acceptance.

14. The X-ray diagnostic apparatus according to claim 10, wherein
the processing circuitry restricts the movement by not starting the movement until the acceptance of information indicating permission of the movement by the permission input circuitry.

15. The X-ray diagnostic apparatus according to claim 10, wherein the X-ray diagnostic apparatus is to be used along with a system for controlling, from outside the inspection room, a device to be inserted into the object and wherein
the processing circuitry accepts instruction by a second user who controls the device.

16. The X-ray diagnostic apparatus according to claim 10, wherein
the permission input circuitry is a switch.

17. The X-ray diagnostic apparatus according to claim 10, wherein
processing circuitry notifies the first user of a content of the movement, for which instruction has been accepted, by creating an image indicating that a movement target moves according to the accepted instruction for the movement, and by causing the image to be displayed on a display provided at a position which is visible to the first user.

18. The X-ray diagnostic apparatus according to claim 10, further comprising:
a light emitting portion provided in at least one location of at least one of the imaging system and the bed of the imaging apparatus, wherein
the processing circuitry makes the light emitting portion emit light toward a moving direction of the movement of the movement target from the light emitting portion provided in the movement target of the movement.

19. A medical image diagnostic system, comprising:
an imaging apparatus including an imaging system and a bed, the imaging system being configured to perform X-ray imaging of an object and being composed of an X-ray source, X-ray detector and a support portion supporting the X-ray source, the bed including a tabletop on which the object is placed;
processing circuitry configured to
accept, from an outside of an inspection room in which the imaging apparatus is provided, an instruction to cause the imaging apparatus to perform an operation, the operation being movement of at least one of the imaging system, the bed and the tabletop, and
notify a content of the movement relating to the accepted instruction to a first user in the inspection room;
permission input circuitry configured to accept information indicating permission of the movement from the first user who has confirmed the content of the movement; and
a remote control system including a remote input circuitry for controlling, from outside the inspection room, a device to be inserted into the object,
wherein the processing circuitry is further configured to cause the imaging apparatus to perform the movement so as to more severely restrict the movement compared with after acceptance of information indicating permission of the movement by the permission input circuitry, until the acceptance of information indicating permission of the movement by the permission input circuitry.

* * * * *